United States Patent [19]
Peinecke et al.

[11] Patent Number: 5,959,190
[45] Date of Patent: Sep. 28, 1999

[54] SENSOR FOR MEASURING THE COMPOSITION OF MIXTURES OF HYDROGEN AND OXYGEN GAS

[75] Inventors: Volker Peinecke; Paul Mohr, both of Stuttgart, Germany

[73] Assignee: Deutsche Forschungsanstalt fuer Luft-und Raumfahrt e.v., Bonn, Germany

[21] Appl. No.: 08/965,108

[22] Filed: Nov. 6, 1997

[30] Foreign Application Priority Data

Nov. 6, 1996 [DE] Germany ............................ 196 45 694

[51] Int. Cl.[6] .................................................. G01N 27/16
[52] U.S. Cl. .......................... 73/25.01; 73/25.04; 422/83; 422/94; 422/95; 422/98; 374/120; 374/129
[58] Field of Search ................. 73/25.01, 25.05; 374/100, 120, 121, 129; 422/83, 94, 95, 98

[56] References Cited

U.S. PATENT DOCUMENTS

| | | |
|---|---|---|
| 1,467,911 | 9/1923 | Arendt et al. . |
| 2,631,925 | 3/1953 | Cohn ................................. 73/25.01 X |
| 3,088,809 | 5/1963 | Boatman ............................. 422/83 X |
| 4,063,898 | 12/1977 | Fisher ................................ 73/25.01 X |
| 5,167,927 | 12/1992 | Karlson ............................. 73/25.03 X |
| 5,360,266 | 11/1994 | Lenfers et al. ..................... 73/25.01 X |

FOREIGN PATENT DOCUMENTS

| | | | |
|---|---|---|---|
| 457660 | 6/1949 | Canada ............................... 73/25.01 |
| 321785 | 6/1989 | European Pat. Off. ............. 73/25.01 |
| 1 176 399 | 8/1964 | Germany . | |
| 38 39 414 | 5/1990 | Germany . | |
| 2103806 | 2/1983 | United Kingdom ................ 73/25.05 |

*Primary Examiner*—Daniel S. Larkin
*Attorney, Agent, or Firm*—Barry R. Lipsitz; Ralph F. Hoppin

[57] ABSTRACT

A sensor is provided for precisely measuring the composition of mixtures of hydrogen and oxygen gas. The sensor has an active surface, at which hydrogen and oxygen are catalytically converted into water. A transport inhibiting barrier is disposed on the active surface. The heat released during the conversion is measured, and is indicative of the mixture composition.

20 Claims, 2 Drawing Sheets

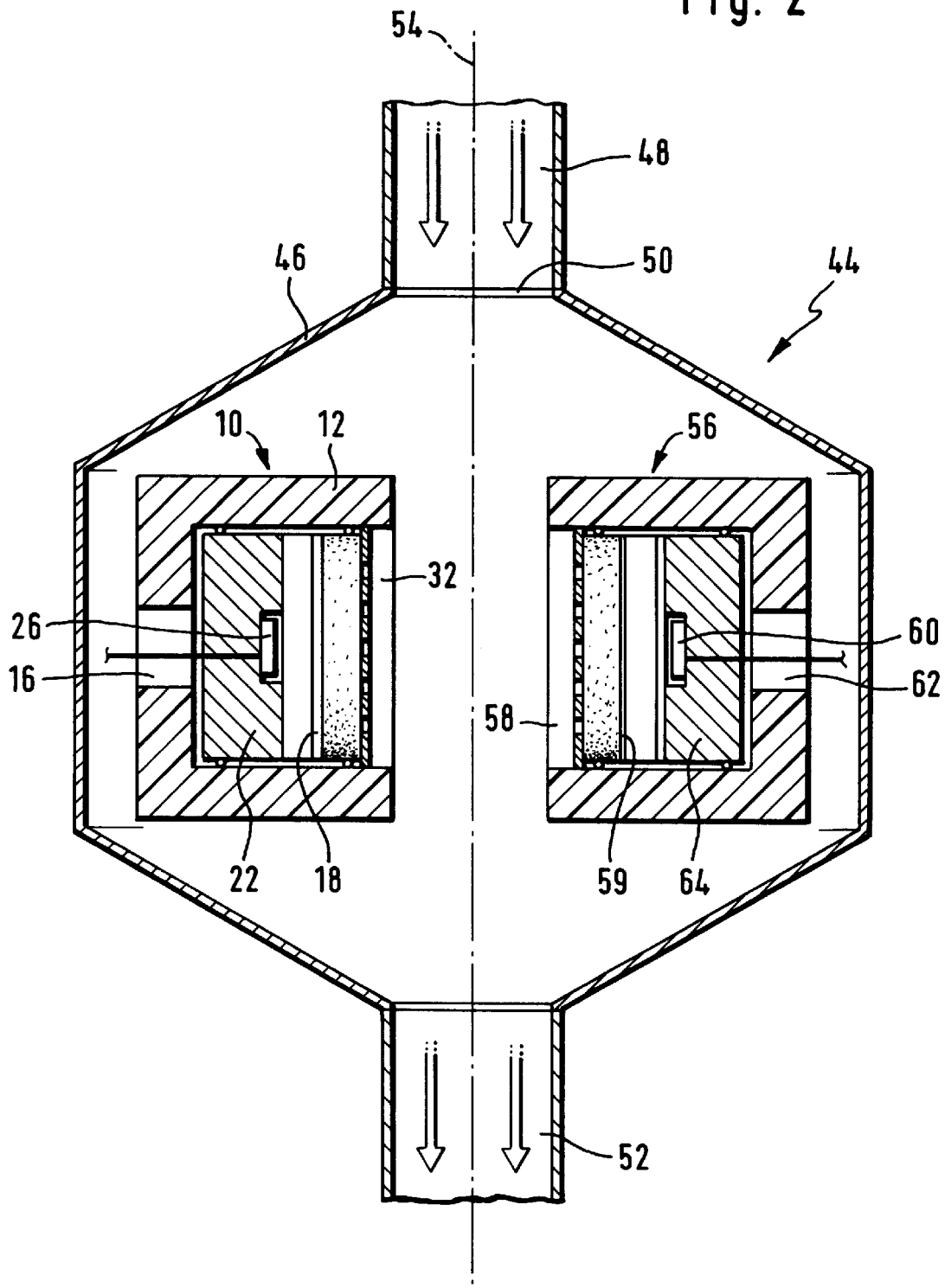

SENSOR FOR MEASURING THE COMPOSITION OF MIXTURES OF HYDROGEN AND OXYGEN GAS

The invention relates to a sensor for measuring the composition of mixtures of hydrogen and oxygen gas.

BACKGROUND OF THE INVENTION

With mixtures of hydrogen and oxygen gas it is necessary constantly to check how high the content of foreign gas or minority gas is, i.e. oxygen in the carrier gas hydrogen or hydrogen in the carrier gas oxygen. If there is too high a concentration of the foreign gas, there is a risk of explosion. The lower explosion limit for mixtures of hydrogen and oxygen is a foreign gas concentration of around 4%. Said foreign gas concentration applies both for hydrogen as a foreign gas in oxygen and for oxygen as a foreign gas in hydrogen.

Electrolysis of water produces hydrogen at the hydrogen cathode and oxygen at the oxygen cathode. However, the hydrogen gas produced always contains a slight amount of oxygen and the oxygen gas produced has a hydrogen content. In the latter case in particular, the foreign gas concentration has to be monitored to ensure that it is a sufficient safety margin below the lower explosion limit in order to avoid a risk of explosion.

SUMMARY OF THE INVENTION

The object of the invention is therefore to provide a sensor which is capable of precisely measuring the composition of mixtures of hydrogen and oxygen gas, is of a simple designs and operates reliably with a high degree of sensitivity.

Said object is achieved with the sensor according to the invention in that the sensor has an active surface, at which hydrogen and oxygen are catalytically convertible into water, and that the heat released during said conversion is measurable by means of a temperature detector.

Because the catalytic reaction may occur at temperatures below or at room temperature, no additional heating is needed for the sensor. It is possible to dispense with gas treatment because the pressure, flow, temperature, and moisture of the measuring gas, whose composition is to be determined, do not have to be adjusted precisely to defined values. Since hydrogen has a high calorific value, the heat released during the conversion of hydrogen and oxygen is relatively high, with the result that even low gas concentrations may be measured by the sensor according to the invention and so the sensor is highly sensitive.

In an advantageous embodiment of the sensor according to the invention, the active surface is formed by a surface of a noble-metal catalyst. Said noble metal may be, for example, platinum or palladium. The active surface, therefore, also has a high thermal conductivity so that the heat released during the conversion of hydrogen and oxygen may be dissipated by means of the active surface.

In a particularly advantageous embodiment, the sensor has a barrier which inhibits or reduces the transport of gas to the active surface. By means of said gas transport-inhibiting barrier, the material transport speed of the measuring gas to the active surface may be controlled and so the sensitivity of the sensor may be fixed.

The gas transport-inhibiting barrier advantageously takes the form of a porous barrier layer so that the measuring gas may diffuse through the porous barrier layer to the active surface. The sensitivity of the sensor may then be controlled by means of the porosity and thickness of the gas transport-inhibiting barrier.

In a constructionally, particularly simple embodiment of a sensor according to the invention, the gas transport-inhibiting barrier is designed in such a way that water produced during the conversion of hydrogen with oxygen at the active surface is removable through the gas transport-inhibiting barrier. There is therefore no need to provide discharge channels in a housing of the sensor. Thus, measuring gas is fed through the gas transport-inhibiting barrier to the active surface and water produced at the active surface is removed through the gas transport-inhibiting barrier. In said case, it is particularly advantageous when the gas transport-inhibiting barrier is designed in such a way that it is not wettable with water, i.e. is of a hydrophobic design. The gas transport-inhibiting barrier is therefore prevented from becoming flooded with water or clogged up and the transport of measuring gas to the active surface is not impeded.

The gas transport-inhibiting barrier is advantageously designed in such a way that it thermally insulates the active surface from an outer chamber or space. As a result, the heat produced at the active surface cannot be dissipated outwards through the gas transport-inhibiting barrier, with the result that the heat effect of the conversion reaction may be measured with great accuracy by the temperature detector.

In a particularly advantageous embodiment, the active surface is in thermal contact with a heat sink or heat distributor.

By said means, the heat released at the active surface may be dissipated and the temperature increase occurring during the exothermic reaction of hydrogen with oxygen may be measured.

In a variant of an embodiment, the active surface is disposed, for example, as a layer on a carrier serving as a substrate, which is in thermal contact with the heat sink. The arrangement on a carrier in particular enables the active surface on the carrier to be given a curved or flat shape.

In order to avoid temperature gradients in the heat sink, the heat sink is advantageously designed in such a way that it ensures a radial temperature compensation in relation to an axis of symmetry of the sensor. As a result, a large amount of the heat released during the conversion of hydrogen and oxygen reaches the temperature detector so that a precise composition of the hydrogen/oxygen mixture is measurable. For said purpose it is particularly advantageous when the temperature detector is disposed in the heat sink. In a variant of an embodiment, the temperature detector is seated in a recess, which is arranged so as to be directed towards the active surface.

The sensor advantageously has a housing of low thermal conductivity, the thermal conductivity of the housing in particular being lower than the thermal conductivity of the heat sink so that the heat released at the active surface is preferably removed in the direction of the heat sink.

For dissipating heat from the heat sink itself, it is advantageous when the housing has one or more openings which are arranged so as to be directed towards the heat sink. By said means, heat may be removed outwards from the heat sink by means of a gas flow and in particular by means of the measuring gas flow which flows around the sensor according to the invention.

A simply designed gas-measuring device for measuring the composition of mixtures of hydrogen and oxygen gas, which is capable of measuring the composition precisely and with a high degree of sensitivity, comprises a sensor having the features described above and the advantages of said features.

In particular, it is advantageous when the gas-measuring device comprises a reference sensor which is used to measure the temperature of the mixture of hydrogen and oxygen gas. By said means, it is possible, during measurement, to eliminate in particular the influence of the temperature of the measuring gas as well as the influence of the moisture of the measuring gas and the flow through the gas-measuring device. In said case, it is particularly advantageous when the sensor and the reference sensor are arranged symmetrically in relation to an axis of symmetry of the gas-measuring device and in particular when the two sensors are arranged symmetrically in relation to a measuring gas supply. As a result, there are identical pressure and flow conditions at the two sensors.

In an advantageous variant of an embodiment, a measuring gas inlet of the sensor is arranged opposite a measuring gas inlet of the reference sensor.

To determine the composition of the mixture, the temperature difference between the temperature measured by the temperature detector of the sensor and the temperature measured by a temperature detector of the reference sensor is determined. Said temperature difference represents the heat tone or heat of reaction effected by the hydrogen/oxygen conversion at the active surface of the one sensor and is substantially independent of the temperature of the measuring gas. By said means, it is possible to determine the composition of the measuring gas with great accuracy. In particular, it is advantageous when the reference sensor is of an identical construction to the sensor, with one component of the reference sensor which corresponds to the active surface of the sensor being made of a material which is catalytically non-active in terms of the hydrogen/oxygen conversion.

DESCRIPTION OF THE PREFERRED EMBODIMENTS

Figure 1:
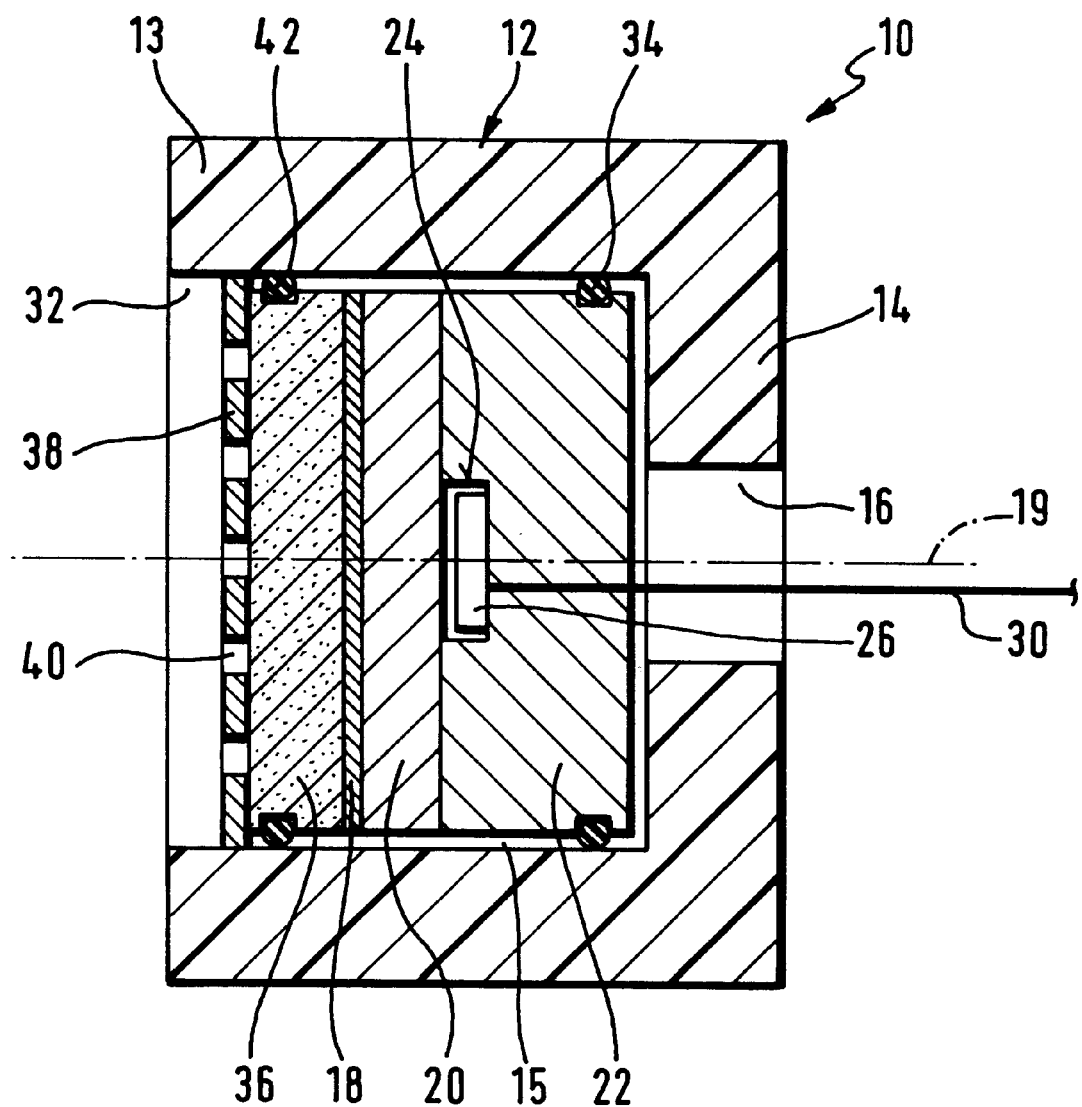
FIG. 1 a section through an embodiment of a sensor according to the invention and FIG. 2 a section through an embodiment of a gas-measuring device according to the invention.

An embodiment of a sensor according to the invention, which is denoted as a whole by 10, is shown in FIG. 1. The sensor 10 has a housing 12. A cavity 15 is formed between housing walls 13 and a housing base 14. The housing base 14 has in its center an opening channel 16. The housing 12 is preferably made of a material of low thermal conductivity, preferably of plastic material.

In the cavity 15, a catalytically active surface 18 is disposed with one surface normal to an axis 19 of the sensor 10, hydrogen and oxygen being converted at said active surface into water in gas or liquid form. The catalytically active surface 18 is preferably the surface of a noble-metal catalyst, such as platinum or palladium. The active surface 18, therefore, has a high thermal conductivity. The active surface 18 is disposed, in the illustrated variant of an embodiment, as a layer on a carrier 20.

The carrier 20 is in thermal contact with a heat sink 22 which dissipates the heat produced at the active surface 18 during the catalytic conversion of hydrogen with oxygen. The heat sink 22 is preferably made of a material of a thermal conductivity which is higher than that of the housing 12 and lower than that of the active surface 18. As a result, a temperature gradient is maintained between the active surface 18 and an outer chamber of the sensor 10 and enables determination of the heat tonality of the catalytic reaction at the active surface 18.

At its end associated with the carrier 20, the heat sink 22 has a recess 24, in which a temperature detector 26, e.g. a thermocouple, is seated. The temperature detector 26 measures, via the temperature, the heat which is produced at the active surface 18 as a result of the conversion of hydrogen and oxygen and is removed via the carrier 20 to the heat sink 22. The heat sink 22 is advantageously designed in such a way that, in relation to the axis 19 of the sensor 10, a good radial equidistribution of the temperature is achievable in the heat sink 22 so that particularly at the temperature detector 26 no radial temperature gradients arise.

The heat sink 22, moreover ensures that heat is removable from the sensor 10. To said end, the opening 16 in the housing 12 is directed towards the heat sink 22. When the sensor 10 is introduced into a gas flow which flows around the sensor 10, the part of the heat sink 22 directed towards the opening 16 then comes into contact with the gas flow. The gas flow may then absorb heat at the heat sink 22 and remove it from the sensor 10.

A line 30 for the temperature signal of the detector 26 leads from the temperature detector 26, through the opening 16 in the housing 12 and into a region outside of the sensor.

At an end of the heat sink 22, remote from a measuring gas inlet opening 32 into the sensor 10, a seal 34, e.g. an O-ring, is disposed between walls of the housing 12 and side walls of the heat sink 22, thereby preventing any gas from penetrating through the opening 16 to the active surface 18.

A gas transport-inhibiting barrier 36 is disposed flat on the active surface 18 of the sensor 10, which may be flat or curved, and is directed towards the inlet opening 32. Seated in front of the gas transport-inhibiting barrier 36 is a retaining grid 38, e.g. in the form of a perforated grid, by means of which the heat sink 22, the carrier 20 with the active surface 18, and the gas transport-inhibiting barrier 36 are held in the housing 12. Measuring gas passes through openings 40 in the retaining grid 38 and through the gas transport-inhibiting barrier 36 to the active surface 18.

The gas transport-inhibiting barrier 36 is of a lower thermal conductivity than the active surface 18 and the carrier 20, so that the active surface 18 is thermally insulated by the gas transport-inhibiting barrier 36 from the inlet opening 32 and hence, from the outer chamber of the sensor 10. A seal 42 between one side of the gas transport-inhibiting barrier 36 and an inside of the housing wall of the housing 12 ensures that measuring gas may reach the active surface 18 only via the gas transport-inhibiting barrier 36. The housing 12 is likewise of a lower thermal conductivity than the active surface 18 and the carrier 20, thereby ensuring that heat may be removed from the active surface 18 only via the heat sink 22.

The active surface 18 is designed in particular as a hydrophilic surface so that it is wettable with the liquid water or water vapour produced during the conversion of hydrogen and oxygen. The gas transport-inhibiting barrier 36, which may in particular take the form of a porous barrier layer, is hydrophobic so that it is not wettable with water. As a result, water produced at the active surface 18 is removable from the sensor 10 via the barrier layer 36 without the barrier layer 36 becoming flooded with water or clogged up. If the gas transport-inhibiting barrier 36 were to become clogged up, the gas transport to the active surface would be interrupted.

The sensor operates as follows:

Measuring gas flows through the openings 40 in the retaining grid 38 to the gas transport-inhibiting barrier 36. The material transport through the barrier layer 36 is effected by means of diffusion, the rate of transport through the barrier layer 36 being all the higher, the higher the concentration of foreign gas, which is the gas present in a lower concentration in the hydrogen/oxygen mixture.

The reaction rate of the catalytic reaction between hydrogen and oxygen effected by the active surface 18 is determined by the concentration of the foreign gas in the carrier gas, which is the gas present in a higher concentration in the hydrogen/oxygen mixture. The heat effect at the catalytic surface 18 is therefore determined by the composition of the hydrogen/oxygen mixture and by means of the temperature, which is measured by the temperature detector 26 and is a measure of the heat conversion, said composition may be determined.

A sensor of the type described above may be used in particular in gas-measuring devices for measuring the composition of mixtures of hydrogen and oxygen gas.

An embodiment of a gas-measuring device, which is denoted as a whole by 44, is shown in FIG. 2. The gas-measuring device 44 comprises a housing 46, leading into which at a mouth 50 is a line 48 for measuring gas, whose composition is to be determined. From the mouth 50, the housing 46 widens and in said widened portion a sensor 10 and a reference sensor 56 are disposed.

The gas flow is removed from the housing 46 by means of a line 52. The housing 46 is preferably symmetrical, in particular axially symmetrical or rotationally symmetrical, in relation to an axis 54.

The sensor 10 is constructed in the manner described above. The inlet opening 32 of the sensor is arranged so as to be directed towards the axis 54. Disposed symmetrically relative to the sensor 10 in relation to the axis 54 is the reference sensor 56, the inlet opening 58 of which is likewise arranged so as to be directed towards the axis 54.

The reference sensor 56 is constructed in an identical manner to the first sensor 10 except that, instead of the active surface 18, a layer 59 is provided which is not catalytically active as regards the hydrogen/oxygen conversion. The layer 59 of the reference sensor 56 is preferably of a similar thermal conductivity to the active surface 18 of the sensor 10. At the reference sensor 56, there is therefore no heat effect as a result of hydrogen/oxygen conversion into water. The reference sensor 56 therefore substantially measures the temperature in the gas flow.

As a measuring signal of the gas-measuring device 44, the difference between the temperature measured by the temperature detector 26 of the sensor 10 and the temperature measured by a temperature detector 60 of the reference sensor 56 is determined. Said measuring signal, which is proportional to the concentration of the foreign gas in the carrier gas, is substantially independent of the temperature of the measuring gas which is fed to the gas-measuring device 44 through the line 48.

Furthermore, by virtue of the symmetrical arrangement of the sensor 10 and the reference sensor 56, the influence of the flow through the gas-measuring device 44 and the influence of the moisture of the measuring gas may be substantially eliminated because there are then identical pressure and flow conditions at both sensors.

It is provided that there is a gap between an end of the housing 12 of the sensor 10 remote from the inlet opening 32 and a wall of the housing 46 of the gas-measuring device 44. An identical gap is provided between the reference sensor 56 and a corresponding housing wall of the housing 46. As a result, the gas flow through the housing 46 may remove heat from the heat sink 22 of the sensor 10 and from a heat sink 64 of the reference sensor 56 by means of the opening 16 in the sensor 10 and an opening 62 in the reference sensor 56 respectively.

What is claimed is:

1. A sensor for measuring the composition of mixtures of hydrogen and oxygen gas, comprising:

an active surface for the catalytic conversion of hydrogen and oxygen into water, said conversion releasing heat measurable by means of a temperature detector; and a barrier disposed on said active surface, said barrier inhibiting the transport of gas to the active surface.

2. A sensor according to claim 1, wherein the active surface comprises a surface of a noble-metal catalyst.

3. A sensor according to claim 1, wherein said barrier comprises a porous barrier layer.

4. A sensor according to claim 1, wherein water produced during the conversion of hydrogen with oxygen at the active surface is removable through said barrier.

5. A sensor according to claim 1, wherein said barrier is not wettable with water.

6. A sensor according to claim 1, wherein said barrier thermally insulates the active surface from an outer chamber.

7. A sensor according to claim 1, wherein said active surface is in thermal contact with a heat sink.

8. A sensor according to claim 7, wherein said active surface is disposed on a carrier which is in thermal contact with said heat sink.

9. A sensor according to claim 7, wherein said heat sink ensures a radial temperature compensation in relation to an axis of symmetry of said sensor.

10. A sensor according to claim 7, wherein said conversion releases heat measurable by means of a temperature detector disposed in the heat sink.

11. A sensor according to claim 10, wherein the temperature detector is seated in a recess arranged so as to be directed towards the active surface.

12. A sensor according to claim 7, further comprising a housing having a thermal conductivity lower than a thermal conductivity of the heat sink.

13. A sensor according to claim 12, wherein said housing has one or more openings arranged so as to be directed towards the heat sink.

14. A gas-measuring device for measuring the composition of mixtures of hydrogen and oxygen gas, comprising:

a sensor having an active surface for the catalytic conversion of hydrogen and oxygen into water, said conversion releasing heat measurable by means of a temperature detector; and a barrier disposed on said active surface, said barrier inhibiting the transport of gas to the active surface.

15. A gas-measuring device according to claim 14, further comprising a reference sensor which is used to measure the temperature of the mixture of hydrogen and oxygen gas.

16. A gas-measuring device according to claim 15, wherein the sensor and the reference sensor are arranged symmetrically in relation to an axis of symmetry of the gas-measuring device.

17. A gas-measuring device according to claim 16, wherein the sensor and the reference sensor are arranged symmetrically in relation to a measuring gas supply.

18. A gas-measuring device according to claim 15, wherein a measuring gas inlet of the sensor is disposed opposite a measuring gas inlet of the reference sensor.

19. A gas-measuring device according to claim 15, wherein the temperature difference between the temperature measured by a temperature detector of the sensor and the temperature measured by a temperature detector of the reference sensor is computed to determine the composition of the mixture.

20. A gas-measuring device according to claim 15, wherein the structure of the reference sensor is identical to the structure of said sensor, except that a component of the reference sensor which corresponds to the active surface of said sensor is constructed of a material that is catalytically non-active with regard to the hydrogen/oxygen conversion.

* * * * *